United States Patent [19]

Larson

[11] Patent Number: 4,591,595

[45] Date of Patent: May 27, 1986

[54] 2-GUANIDINO-4-(2-METHYL-4-IMIDAZOLYL)THIAZOLES IN THE TREATMENT OF RHEUMATOID ARTHRITIS

[75] Inventor: David L. Larson, East Lyme, Conn.

[73] Assignee: Pfizer Inc., New York, N.Y.

[21] Appl. No.: 763,730

[22] Filed: Aug. 9, 1985

Related U.S. Application Data

[63] Continuation-in-part of Ser. No. 659,750, Oct. 11, 1984, abandoned.

[51] Int. Cl.⁴ .......................................... A61K 31/425
[52] U.S. Cl. ..................................................... 514/367
[58] Field of Search ......................................... 514/367

[56] References Cited

U.S. PATENT DOCUMENTS 4,374,843  2/1983  LaMattina et al. ............... 424/270

Primary Examiner—Stanley J. Friedman
Attorney, Agent, or Firm—Charles J. Knuth; Albert E. Frost; Robert K. Blackwood

[57] ABSTRACT

2-Guanidino-4-(2-methyl-4-imidazolyl)thiazole and 2-(N-pentyl-N'-guanidino)-4-(2-methyl-4-imidazolyl)-thiazole, histamine-$H_2$ antagonist useful as a gastric acid antisecretory and antiulcer agents, are also useful per se in the treatment of rheumatoid arthritis.

4 Claims, No Drawings

2-GUANIDINO-4-(2-METHYL-4-IMIDAZOLYL)-THIAZOLES IN THE TREATMENT OF RHEUMATOID ARTHRITIS

CROSS REFERENCE TO RELATED APPLICATION

This application is a continuation-in-part of copending U.S. patent application, Ser. No. 659,750, filed Oct. 11, 1984, now abandoned.

BACKGROUND OF THE INVENTION

The present invention is directed to the use of 2-guanidino-4-(2-methyl-4-imidazolyl)thiazole, 2-(N-pentyl-N'-guanidiano)-4-(2-methyl-4-imidazolyl)thiazole and analogs (or pharmaceutically acceptable salts thereof) in the treatment of rheumatoid arthritis. In spite of the wide use of steroidal and nonsteroidal antiinflammatory agents, rheumatoid arthritis remains an inadequately treated disease. For example, in many individuals, the gastrointestinal side effects associated with said antiinflammatory agents effectively prevents their use. Thus, present use of 2-guanidino-4-(2-methyl-4-imidazolyl)thiazole and its N-pentyl analog, lacking such gastrointestinal side effects, represents a valuable addition to the physician's aramentarium of agents for the treatment of rheumatoid arthritis.

2-Guanidino-4-(2-methyl-4-imidazolyl)thiazole, analogs, and pharmaceutically acceptable salts thereof have been previously reported as histamine-$H_2$ antagonists, and so are useful as gastric acid antisecretory and antiulcer agents; LaMattina and Lipinski, U.S. Pat. No. 4,374,843 (1983). An improved method for the preparation of 2-guanidino-4-(2-methyl-4-imidazolyl)-thiazole and its salts, in particular the dihydrochloride preferred for use in the present invention, is also disclosed hereinafter in specific examples below.

2-(N-Pentyl-N'-guanidino)-4-(2-methyl-4-imidazolyl)-thiazole is the subject of copending U S. application of Reiter, Ser. No. 605,510, filed April 30, 1984, for "2-(N-Substituted guanidino)-4-heteroarylthiazole Antiulcer Agents." The method of preparing said N-pentylguanidino compound and employing same as an antiulcer and/or as a gastric antisecretory agent is also detailed hereinafter.

SUMMARY OF THE INVENTION

The present invention is directed to a method of treating rheumatoid arthritis suffered by a mammal, including man, which comprises administration of an antirheumatoid arthritis amount of 2-guanidino-4-(2-methyl-4-imidazolyl)thiazole, 2-(N-pentyl-N'-guanidino)-4-(2-methyl-4-imidazolyl)thiazole, or a pharmaceutically acceptable salt thereof. The preferred route of administration is oral. The preferred forms of 2-guanidino-4-(2-methyl-4-imidazolyl)thiazole and its N-pentyl analog are their dihydrochloride salts, whose preparation was generally disclosed by LaMattina et al. and Reiter (cited above) and is specifically described below.

The present invention is also directed to a unit dosage form comprising an antirheumatoid arthritis amount of 2-guanidino-4-(2-methyl-4-imidazolyl)thiazole, its N-pentyl analog, or a pharmaceutically acceptable salt thereof in the form of a tablet or capsule suitable for oral use in a mammal, including man.

DETAILED DESCRIPTION OF THE INVENTION

The clinical utility of 2-guanidino-4-(2-methyl-4-imidazolyl)thiazole and its N-pentyl analog in the treatment of rheumatoid arthritis in man is reflected by laboratory studies demonstrating its beneficial effect against the secondary response in adjuvant-induced arthritis in rats. A typical protocol for these studies is described in specific examples below, in which is seen the beneficial effect of 2-guanidino-4-(2-methyl-4-imidazolyl)thiazole alone on the course of adjuvant arthritis in rats. Included in these examples are control studies with antiinflammatory piroxicam.

For the purpose of the present specification and claims, a method of treating arthritis with an antirheumatoid arthritis amount of the present active agent is meant to include an amount sufficient to relieve the immediate symptoms of said rheumatoid arthritis and to alleviate the advance of the disease. To this end, 2-guanidino-4-(2-methyl-4-imidazolyl)thiazole, its N-pentyl analog, and the pharmaceutically acceptable salts thereof are administered to a subject suffering from rheumatoid arthritis by a variety of conventional routes of administration including orally and parenterally. Preferably, these compounds are administered orally. In general, they will be administered orally at doses between about 0.1 and 20 mg/kg body weight of the subject to be treated per day, preferably from about 0.2 to 2.5 mg/kg per day. If parenteral administration is desired, then these compounds are given at doses between 0.1 and 1.0 mg/kg body weight of the subject to be treated per day. However, some variation in dosage will necessarily occur depending upon the condition of the subject being treated, at the descretion of the attending physician.

The compound is administered alone or in combination with pharmaceutically acceptable carriers or diluents, in either single or multiple doses. Suitable pharmaceutical carriers include inert diluents or fillers, sterile aqueous solutions and various organic solvents. The pharmaceutical compositions formed by combining 2-guanidino-4-(2-methyl-4-imidazolyl)thiazole, its pentyl analog, or salt thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, may be employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof. Preferably, 2-guanidino-4-(2-methyl-4- imidazolyl)thiazole or salt is administered orally, in a solid, unit dosage form, i.e. as a single physically discrete dosage unit containing an appropriate amount of the active compound in combination with a pharmaceutically acceptable carrier or diluent. Particular examples of such unit dosage forms are tablets or capsules containing from about 5 to 1,000 mg of the active ingredient, comprising from about 10% to 90% of the total weight of the dosage unit.

For parenteral administration, a suspension or solution of 2-guanidino-4-(2-methyl-4-imidazolyl)-thiazole, its pentyl analog, or salt thereof in sterile aqueous media, for example aqueous propylene glycol, sodium chloride, dextrose or sodium bicarbonate solutions are employed. Such solutions are suitably buffered if necessary and the liquid diluent usually rendered isotonic with sufficient saline or glucose. The preparation of suitable sterile liquid media for parenteral administration will be well known to those skilled in the art.

The present invention is illustrated by the following examples. However, it should be understood that the invention is not limited to the specific details of these examples.

EXAMPLE 1

2-Guanidino-4-(2-methyl-4-imidazolyl)thiazole (Free Base)

2-Guanidino-4-(2-methyl-4-imidazolyl)thiazole monohydrobromide (360.7 g, 1.19 mole; U.S. Pat. No. 4,374,843) was slurried in 7500 ml $H_2O$ for 15 minutes at 19° C. With stirring, the pH was slowly adjusted from 5.8 to a stable value of 9.5 with 10% NaOH, 500% 5 ml being required. After stirring a further 0.5 hours, title product was recovered by filtration on sintered glass. The sticky cake was washed with 2000 ml $H_2O$, pulled to a tight cake and finally washed with 1000 ml of hexane. After air drying on the funnel for 18 hours, the entire still-partially-wet cake was taken into the next step.

If required for formulation, the free base is dried to constant weight in vacuo, correcting for any remaining water in the formulation.

EXAMPLE 2

2-Guanidino-4-(2-methyl-4-imidazolyl)thiazole Dihydrochloride

The entire batch of partially-wet, free base of the preceding Example, presumed to contain the theoretical 265.3 g of free base on an anhydrous basis, was combined with 1030 ml of $CH_3OH$ and 4125 ml of isopropanol and heated to reflux. The hot solution was treated with 62 g activated carbon. After refluxing for 30 minutes, the hot mixture was filtered over diatomaceous earth with 2750 ml of hot isopropanol for wash. The combined filtrate and wash was diluted with an additional 2750 ml of isopropanol, now at 60° C. With stirring, concentrated HCl (345 ml) was added in a thin stream. The resulting suspension was concentrated to 2750 ml in vacuo, chased with 5500 ml of isopropanol while maintaining that volume, cooled to 0°–5° C., stirred 1.5 hours at that temperature, and title product recovered by filtration, washed with 700 ml cold isopropanol and dried in vacuo at ambient temperature; 307.2 g (87%) over two steps, m/e 222; u.v. lambda max. (0.01N HCl/$CH_3OH$) 229 and 260 nm ($E_{1cm}^{1\%}$ 661 and 569); lambda max. (0.01N NaOH/$CH_3OH$) 248 and 274 nm ($E_{1cm}^{1\%}$ 681 and 475); neutralization equivalent (1:1 ethanol:$H_2O$ with 0.5N NaOH) calcd. 295.2; found 299.9. Analysis calculated for $C_8H_{10}N_6S.2HCl$: C,32.55; H, 4.10; N, 28.47; S, 10.86; $Cl^-$, 24.02%. Found: C, C, 32.30; H, 4.06; N, 28.29; S, 11.05; $Cl^-$, 24.05%.

Alternatively, free base (10.0 g, 0.045 mol, weight corrected for up to 20% water content) was dissolved in 100 ml of hot glacial acetic acid, an amount just sufficient for complete dissolution at near reflux temperature. The hot solution was diluted with 10 ml additional hot acetic acid and then 7.5 ml (0.090 mol) of concentrated HCl was added. Title product, which began to crystallize almost immediately, was recovered by filtration after cooling to room temperature, and dried in vacuo at 40° C.; yield 12.63 g (95%), identical with the product crystallized from isopropanol.

Alternatively, free base (1.0 g, 0.0045 mol) was dissolved in 2 ml concentrated HCl. The dihydrochloride crystallized almost immediately. The mixture was diluted with 5 ml acetone, stirred 5 minutes, and title product recovered by filtration with acetone wash, 1.15 g (86.6%), identical with the product of Method A above. Analysis calculated for $C_8H_{10}N_6S.2HCl$: C, 32.55; H, 4.10; N, 28.47%. Found: C, 32.16; H, 4.40; N, 28.09%.

EXAMPLE 3

2-Guanidino-4-(2-methyl-4-imidazolyl)thiazole Dihydrobromide

Method A

2-Methyl-4-acetylimidazole (4.00 g, 0.0322 mol; U.S. Pat. No. 4,374,843) was dissolved in 48% HBr (40 ml, 0.351 mol), the temperature rising to 33° C. The solution was heated to 50° C. $Br_2$ (1.65 ml, 5.15 g, 0.0322 mol) in 5 ml of 48% HBr was added dropwise over 17 minutes maintaining that temperature with external heating as necessary. The stirred reaction mixture was heated to 65° C. for 1.5 hours, cooled and stripped to a cream-colored slurry. The mixture was chased 2×20 ml $H_2O$ (the solids dissolving and returning to a thick slurry each time). Without further isolation of the intermediate 2-methyl-4-(bromoacetyl)imidazole, absolute ethanol (29.2 ml) was added, and then N-amidinothiourea (3.81 g, 0.0322 mol) and the slurry heated to reflux. The resulting solution was refluxed for 2 hours, by which time there was heavy precipitation of crystalline title product. The slurry was distilled to half-volume, cooled to room temperature, and title product recovered by filtration with a small amount of ethanol wash and dried at 35° C. in vacuo; 10.12 g (79% over two chemical steps); homogeneous by tlc Rf 0.75 (19:1 ethanol:concentrated $NH_4OH$); m.p. 300° C. (decomposition). Analysis calculated for $C_8H_{10}N_6S.2HBr.0.5H_2O$: C, 24.44; H, 3.33; N, 21.38%. Found: C, 24.20; H, 3.18; N, 21.43%.

Method B

In the manner of Method A, 2-methyl-4-acetylimidazole (4.00 g, 0.0322 mol) was brominated, but with substitution of 3.67 ml (0.0322 mol) of 48% HBr and 4 ml of acetic acid for the initial charge of 48% HBr, and charging the $Br_2$ (1.65 ml) in 4 ml of acetic acid in place of 48% HBr. At the end of the 1.5 hour heating period (*without* cooling, stripping and chasing), the N-amidinothiourea (3.81 g) was added. The reaction exothermed from 67 to 77° C., and the resulting solution was heated at 80° C. for 1 hour during which title product began to precipitate heavily. Title product was recovered as in Method A, 9.34 g (73% over two chemical steps), identical with the product of Method A.

Method C

To 48% HBr (16.9 ml) was added 2-methyl-4-acetyl-imidazole (7.36 g, 0.059 mol) to form a clear yellow solution. Br$_2$ (3.0 ml, 0.059 mol) in 48% HBr (3.3 ml) was added dropwise as the reaction was warmed to 45° C. Transient precipitation was noted during addition and heating. After stirring for 18 hours at 45° C., the reaction mixture was cooled to 30° C., diluted with 22 ml absolute ethanol, and N-amidinothiourea (7.0 g) was added. The resulting slurry almost became clear, then set up to solids which were broken up with a spatula. The resulting mobile slurry was stirred at 55° C. for 2 hours, cooled to 10° C., and title product recovered by filtration with 2×5 ml absolute ethanol wash, 20.3 g (86%), identical with title product of Method A.

EXAMPLE 4

2-Guanidino-4-(2-methyl-4-imidazolyl)thiazole (Free Base)

2-Guanidino-4-(2-methyl-4-imidazolyl)thiazole dihydrobromide (13.4 g) was stirred with 66.9 ml H$_2$O and the pH slowly adjusted to a stable value of 10.0 over 2 hours with 22.6 ml of 3N NaOH while maintaining a temperature of 22°–24° C. Title product was recovered by suction filtration with water wash, pulled to a tight cake under a rubber dam, repulped in 28 ml acetone for 2 hours, refiltered, washed with 12 ml acetone and dried at 40° C. in vacuum to yield crystalline title product, 8.66 g, containing about 15% water.

Anhydrous free base was prepared from water-wet cake (prepared as above, without acetone repulp) by dissolving 4.04 g of the water-wet cake (estimated to contain 1.60 g of free base on a dry basis) in 80 ml of refluxing acetone, treating the solution with 0.16 g activated carbon, filtering hot, concentrating the filtrate to 15 ml, stirring at room temperature for 1 hour, filtering with acetone wash and drying the cake at 40° C. in vacuo; yield: 1.57 g.

EXAMPLE 5

4-(2-Methyl-4-imidazolyl)-2-(N-pentyl-N-guanidino)thiazole Dihydrochloride (N-pentylguanyl)thiourea (21.12 g, 0.112 mol) and 4-bromoacetyl-2-methylimidazole hydrobromide (27.65 g, 0.097 mol) were combined in acetone (400 ml) and refluxed for 24 hours. The resulting solid was collected, washed with acetone and dried yielding 40.63 g (92.2%) of light yellow dihydrobromide salt of the desired product.

Dihydrobromide salt (81.14 g, 0.179 mol) was dissolved in warm water (1500 ml) and added slowly to a solution of sodium carbonate monohydrate (88.6 g, 0.714 mol) in water (800 ml). After complete addition the mixture was stirred for 30 minutes and was then filtered. The filter cake was washed thoroughly with water and dried in vacuo for 48 hours. This solid was dissolved in acetone (2 l), filtered to remove small amounts of suspended material, acidified with conc. HCl (34 ml, 0.408 mol) and diluted with additional acetone (1 l). The resulting precipitate was collected, washed and dried yielding 62.44 g (93.2%) of off-white solid, mp 299°–301°.

Anal. Calcd. for $C_{13}H_{20}N_6S \cdot 2HCl \cdot 0.5H_2O$: C, 41.71; H, 6.19; N, 22.45; Cl$-$, 19.41. Found: C, 41.75; H, 6.21; N, 22.42; Cl$-$, 19.03.

EXAMPLE 6

The Effect of 2-Guanidino-4-(2-methyl-4-imidazolyl)thiazole on the Course of Adjuvant-Induced Arthritis in the Rat Adjuvant arthritis was induced in adult male Wistar-Lewis rats weighing 250–270 grams each (Charles River Breeding Laboratories, Kingston, N.Y.) by a single subplantar injection of 1 mg of *Mycobacterium butyricum* (Difco Laboratories, Lot #0640-33) suspended in 0.1 ml mineral oil as described by Walz et al. (Proc. Soc. Exptl. Biol. Med., 136: 907–910, 1971). Seven rats were used in each group. Orally administered drugs were dissolved in water and dilute sodium hydroxide was added as necessary to ensure solution; control groups received only water. After neutralization of the solutions to pH 7.0, a volume of 10 ml/kg body weight was given by intubation with a blunt end, 18-gauge needle. Doses of each drug were given daily starting 1 day before the injection of adjuvant and continuing until 16 days after the induction of the arthritic lesion.

The initial hindpaw volumes (Vi) were measured on the day of adjuvant injection and the resultant swelling was determined on the injected paw (Vf - Vi) on the 4th day following the adjuvant injection. This was considered to be the *primary* response or lesion. The swelling (Vf - Vi) measured 16 days after adjuvant injection on the contralateral, non-injected hindpaw constituted the *secondary* response or lesion. The rats were weighed at the start of the experiments as well as 4 and 16 days after the induction of the disease. Percent inhibition of edema was calculated according to the following formula:

$$\% \text{ Inhibition of Edema} = 1 - \left[ \frac{Vf \text{ drug} - Vi \text{ drug}}{Vf \text{ control} - Vi \text{ control}} \right] \times 100$$

Results are shown in Table I. As calculated by linear regression analysis, the data in Table I show that piroxicam alone showed a correlation coefficient (r) of 0.95 and an ED$_{50}$ of 2.60 mg/kg against primary lesions; and r=1.00 and ED$_{50}$=0.45 mg/kg against secondary lesions. For 2-guanidino-4-(2-methyl-4-imidazolyl)thiazole, no significant activity was noted for primary lesions; while significant activity against secondary lesions was noted, no reliable ED$_{50}$ could be extrapolated from this data.

TABLE I

The Comparative Effect of Piroxicam and 2-Guanidino-4-(2-methyl-4-imidazolyl)thiazole (Compound A) on Adjuvant-Induced Arthritis

| Oral Dose (mg/kg) | | % Inhibition of Lesions $\bar{X}$ +/− (SE)* | |
|---|---|---|---|
| Piroxicam | Compound A*** | Primary | Secondary |
| 0.10 | — | 29 (4)** | 26 (2)** |
| 0.33 | — | 33 (8)** | 43 (4)** |
| 1.00 | — | 45 (7)** | 64 (3)** |
| — | 1.0 | 0 (6) | 3 (3) |
| — | 3.3 | 0 (3) | 28 (4)** |
| — | 10.0 | 2 (2) | 27 (3)** |

* = Mean value of inhibition of edema +/− standard error; 21 rats were used in each dose of piroxicam (14 as the free enol, 7 as the ethanolamine salt); 7 rats were used for each of the two lower doses of compound A, and 14 rats for the 10 mg/kg dose.
** = Significantly different (p << 0.05) from non-treated arthritic rats as determined by Student's t-test for non-paired data.
*** = As the dihydrochloride salt.

PREPARATION 1

N-Pentyl-N'-cyanoguanidine

Pentylamine (17.43 g, 0.20 mol) in 2-propanol (175 ml) was acidified with conc. HCl (17 ml, 0.204 mol) and then treated with sodium dicyanamide (23.15 g, 0.26 mol). The mixture was refluxed for 20 hours, allowed to cool and filtered through diatomaceous earth. The filtrate was concentrated in vacuo and the residue dissolved in chloroform. This solution was washed with water and dried over magnesium sulfate. Filtration and evaporation in vacuo gave 20.93 g (67.9%) of off-white solid; mass spec.: M+ at 154.

PREPARATION 2

(N-Pentylguanyl)thiourea

N-Pentyl-N'-cyanoguanidine (30.0 g, 01.95 mol) and diethylamine (3 ml) were combined in methanol (550 ml). This solution was cooled to $-40°$, saturated with hydrogen sulfide gas, transferred to a stainless steel bomb and heated at 85° for 40 hours. The excess hydrogen sulfide was purged from the reaction mixture with nitrogen and the solution was then concentrated in vacuo. The residue was flash chromatographed (140 mm column, 5% methanol in chloroform). The fractions containing pure product were combined and evaporated yielding 22.01 g (59.9%) of white solid. A portion was recrystallized from chloroform to furnish material with mp 98°–100° ; mass spec.: M+ 188.

I claim:

1. A method of treating rheumatoid arthritis in a mammal suffering from said rheumatoid arthritis which comprises administering to said mammal an antirheumatoid arthritis amount of a compound which is 2-guanidino-4-(2-methyl-4-imidazolyl)thiazole, 2-(N-pentyl-N'-guanidino)-4-(2-methyl-4-imidazolyl)-thiazole, or a pharmaceutically acceptable salt thereof.

2. A method of claim 1 wherein the route of administration is oral.

3. A method of claim 1 wherein the compound is 2-guanidino-4-(2-methyl-4-imidazolyl)thiazole in the form of its dihydrochloride salt.

4. A method of claim 3 wherein the route of administration is oral.

* * * * *